(12) United States Patent
Bauer et al.

(10) Patent No.: US 6,388,119 B1
(45) Date of Patent: May 14, 2002

(54) PREPARATION OF ORGANOSILANES

(75) Inventors: Andreas Bauer; Oliver Schäfer, both of München; Markus Kriegbaum, Sauerlach; Leonhard Brader, Fischbachau; Bernd Pachaly, Mehring-Öd; Volker Frey, Burghausen, all of (DE)

(73) Assignee: Consortium fur elektrochemische Industrie GmbH, Munich (DE)

( * ) Notice: Subject to any disclaimer, the term of this patent is extended or adjusted under 35 U.S.C. 154(b) by 0 days.

(21) Appl. No.: 09/966,822

(22) Filed: Sep. 27, 2001

(30) Foreign Application Priority Data

Oct. 26, 2000 (DE) .......................... 100 53 037

(51) Int. Cl.$^7$ ................................. C07F 7/08
(52) U.S. Cl. ...................................... 556/479
(58) Field of Search ......................... 556/479

(56) References Cited

U.S. PATENT DOCUMENTS 4,658,050 A * 4/1987 Quirk et al. ................ 556/479
5,616,762 A * 4/1997 Kropfgans et al. ......... 556/479
6,271,280 B1 * 8/2001 Boileau et al. ............ 556/479 X
6,303,728 B1 * 10/2001 Hagimori et al. ........ 556/479 X

* cited by examiner

*Primary Examiner*—Paul F. Shaver
(74) *Attorney, Agent, or Firm*—Brooks & Kushman P.C.

(57) ABSTRACT

The invention relates to a process for preparing a silane of the formula I $$R^6R^5CH-R^4CH-SiR^1R^2R^3 \qquad (I),$$

which comprises reacting a silane of the formula II $$HSiR^1R^2R^3 \qquad (II),$$

with an alkene of the formula III $$R^6R^5CH=CHR^4 \qquad (III),$$

in the presence of an iridium compound of the formula IV as catalyst $$[(\text{diene})\text{IrCl}]_2 \qquad (IV),$$

and free diene as cocatalyst, where $R^1$, $R^2$, $R^3$, $R^4$, $R^5$, $R^6$, R and diene are as defined in claim 1.

18 Claims, No Drawings

PREPARATION OF ORGANOSILANES

BACKGROUND OF THE INVENTION

1. Field of the Invention

The invention relates to a process for preparing organosilanes by hydrosilylation in the presence of an iridium compound as catalyst and free diene as cocatalyst.

2. Background Art

Substituted alkylsilanes are of tremendous economic importance in many fields. They are used, for example, as adhesion promoters and as crosslinkers.

The platinum- or rhodium-catalyzed hydrosilylation of unsaturated compounds has been widely studied in the past. The product yields are often very low, being only 20–45%, which is attributable to considerable secondary reactions.

Iridium catalysts containing diene ligands are, according to U.S. Pat. No. 4,658,050, used in the hydrosilylation of allyl compounds by means of alkoxy-substituted silanes. JP-A-07126271 describes the hydrosilylation of allyl halides using chlorodimethylsilane in the presence of iridium catalysts containing diene ligands. Disadvantages of these processes are either moderate yields, an uneconomically high catalyst concentration and/or a very short catalyst life.

SUMMARY OF THE INVENTION

It is an object of the invention to develop a catalyst system which has a long life, which ensures high product yields and purities when using very small amounts of catalyst, and which further allows both continuous and batchwise operation.

DETAILED DESCRIPTION OF THE PREFERRED EMBODIMENT

The invention provides a process for preparing a silane of the formula I $$R^6R^5CH—R^4CH—SiR^1R^2R^3 \quad (I),$$

which comprises reacting a silane of the formula II $$HSiR^1R^2R^3 \quad (II),$$

with an alkene of the formula III $$R^6R^5CH=CHR^4 \quad (III),$$

in the presence of an iridium compound of the formula IV as catalyst $$[(diene)IrCl]_2 \quad (IV),$$

and free diene as cocatalyst, where $R^1$, $R^2$, and $R^3$ are each independently a monovalent Si—C-bonded, unsubstituted or halogen-substituted $C_1$–$C_{18}$-hydrocarbon radical, a chlorine atom or a $C_1$–$C_{18}$-alkoxy radical, $R^4$, $R^5$, and $R^6$ are each independently a hydrogen atom, a monovalent $C_1$–$C_{18}$-hydrocarbon radical which may be unsubstituted or may optionally bear F, Cl, OR, $NR'_2$, CN or NCO atoms/groups as substituents, a chlorine atom, a fluorine atom or a $C_1$–$C_{18}$-alkoxy radical, where in each case 2 radicals $R^4$, $R^5$, $R^6$ together with the carbon atoms to which they are bound may form a cyclic radical, R is a hydrogen atom or a monovalent $C_1$–$C_{18}$-hydrocarbon radical and diene is a $C_4$–$C_{50}$-hydrocarbon compound which may be unsubstituted or bear F, Cl, OR, $NR'_2$, CN or NCO atoms/groups as substituents and has at least two ethylenic C=C double bonds.

In this process, the target products of the formula I are typically obtained in yields of from 95% to 98% when using very small amounts of catalyst. Depending on the field of application, work-up by distillation can therefore often be dispensed with.

$C_1$–$C_{18}$-hydrocarbon radicals $R^1$, $R^2$, $R^3$ are preferably alkyl, alkenyl, cycloalkyl or aryl radicals. $R^1$, $R^2$, $R^3$ preferably have not more than 10, in particular not more than 6, carbon atoms. $R^1$, $R^2$, $R^3$ are preferably linear or branched $C_1$–$C_6$-alkyl radicals or $C_1$–$C_6$-alkoxy radicals. Preferred halogen substituents are fluorine and chlorine. Particularly preferred radicals $R^1$, $R^2$, $R^3$ are methyl, ethyl, methoxy, ethoxy, chlorine, phenyl and vinyl.

Hydrocarbon radicals $R^4$, $R^5$, $R^6$ are preferably alkyl, alkenyl, cycloalkyl or aryl radicals. It is preferred that not more than one of $R^4$, $R^5$, $R^6$ is an alkoxy radical. $R^5$, $R^6$ preferably have not more than 10, in particular not more than 6, carbon atoms. $R^5$, $R^6$ are preferably linear or branched $C_1$–$C_6$-alkyl radicals or $C_1$–$C_6$-alkoxy radicals. Particularly preferred radicals $R^5$, $R^6$ are hydrogen, methyl, ethyl, chlorine and phenyl.

The hydrocarbon radical $R^4$ preferably has not more than 6, in particular not more than 2, carbon atoms. Particularly preferred radicals $R^4$ are hydrogen, methyl, and ethyl.

The hydrocarbon radical R preferably has not more than 6, in particular not more than 2, carbon atoms.

The hydrocarbon compounds used as diene may comprise not only molecular units containing the ethylenic C=C double bonds, but may also comprise alkyl, cycloalkyl or aryl units. The dienes preferably have from 6 to 12 carbon atoms. Preference is given to monocyclic or bicyclic dienes. Preferred examples of dienes are butadiene, 1,3-hexadiene, 1,4-hexadiene, 1,5-hexadiene, isoprene, 1,3-cyclohexadiene, 1,3-cyclooctadiene, 1,4-cyclooctadiene, 1,5-cyclooctadiene and norbornadiene.

The diene in the catalyst of the formula IV and the free diene serving as cocatalyst can be identical or different. Preference is given to the two dienes being identical.

In a particularly preferred case, the catalyst of the formula IV used is $[(cycloocta-1c,5c-diene)IrCl]_2$ and the cocatalyst used is 1,5-cyclooctadiene.

The silane component of the formula II is preferably used in an excess of from 0.01 to 100 mol % of II, more preferably from 0.1 to 10 mol %, based on the alkene of the formula III. The iridium compound of the formula IV is preferably present in a concentration of from 5 to 250 ppm, in particular from 10 to 50 ppm, based on all components present in the reaction mixture. The diene as cocatalyst is preferably added in a concentration of from 50 to 2500 ppm, in particular from 50 to 1000 ppm, based on all components present in the reaction mixture.

The process can be carried out in the presence or absence of aprotic solvents. If aprotic solvents are used, solvents or solvent mixtures having a boiling point or boiling range up to 120° C. at 0.1 MPa are preferred. Examples of such solvents are ethers such as dioxane, tetrahydrofuran, diethyl ether, diisopropyl ether, and diethylene glycol dimethyl ether; chlorinated hydrocarbons such as dichloromethane, trichloromethane, tetrachloromethane, 1,2-dichloroethane, and trichloroethylene; hydrocarbons such as pentane, n-hexane, hexane isomer mixtures, heptane, octane, naphtha, petroleum ether, benzene, toluene, and xylene(s); ketones such as acetone, methyl ethyl ketone, diisopropyl ketone, and methyl isobutyl ketone (MIBK); esters such as ethyl acetate, butyl acetate, propyl propionate, ethyl butyrate, and ethyl isobutyrate; carbon disulfide; and nitrobenzene, or mixtures of these solvents. This list is exemplary and not limiting.

The target product of the formula I can also be used as an aprotic solvent in the process. This process variant is preferred. For example, the reaction components of the formula II together with the iridium catalyst of the formula IV and optionally the diene are placed in a reaction vessel and the reaction component of the formula III, optionally in admixture with the diene, is introduced while stirring. In another variant, the target product of the formula I together with the catalyst of the formula IV and optionally diene are placed in a reaction vessel and a mixture of components II, III and optionally diene is introduced. The reaction time to be employed is preferably from 10 to 2000 minutes. The reaction is preferably carried out at a temperature of from 0 to 300° C., in particular from 20 to 200° C. The use of superatmospheric pressure may also be useful; the pressure is preferably up to 100 bar.

The addition of the diene also allows a plurality of reactions to be carried out without further addition of catalyst. Preference is given to adding further amounts of diene as cocatalyst as the reaction proceeds, in particular, in a continuous manner.

The meanings of all the symbols in the formulae above are in each case independent of one another. In the following examples, all concentrations and percentages are by weight, all pressures are 0.10 MPa (abs.) and all temperatures are 20° C. unless indicated otherwise.

EXAMPLE 1
(Embodiment I)

19.2 g (0.25 mol) of allyl chloride, 0.1 g ($9.2 \cdot 10^{-4}$ mol) of 1,5-cyclooctadiene and 3.0 mg ($4.5 \cdot 10^{-6}$ mol) of di-$\mu$-chlorobis[(cycloocta-1c,5c-diene)iridium(I)] were placed in a 100 ml three-neck flask provided with a low-temperature condenser, internal thermometer and dropping funnel. At a bath temperature of 37° C., a mixture of 23.7 g (0.25 mol) of chlorodimethylsilane and 0.1 g ($9.2 \cdot 10^{-4}$ mol) of 1,5-cyclooctadiene was introduced over a period of 1.5 hours in such a way that the internal temperature did not exceed 45° C. For the post-reaction, the mixture was maintained at a bath temperature of 45° C. for an additional one hour. Work-up by distillation gave 40.8 g of chloro(3-chloropropyl)dimethylsilane, corresponding to a yield of 95% based on the silane.

EXAMPLE 2
(Reusability of a Catalyst Charge)

The procedure was analogous to that of Example 1. In place of the work-up by distillation, 19.2 g (0.25 mol) of allyl chloride and 0.1 g ($9.2 \cdot 10^{-4}$ mol) of 1,5-cyclooctadiene were added to the mixture and a mixture of 23.7 g (0.25 mol) of chlorodimethylsilane and 0.1 g ($9.2 \cdot 10^{-4}$ mol) of 1,5-cyclooctadiene was again introduced. The reaction was carried out in a manner analogous to Example 1. The total yield after distillation was 76.2 g (89%).

EXAMPLE 3
(Demonstration of the Catalytic Activity of the Distillation Bottoms)

19.2 g (0.25 mol) of allyl chloride and 0.1 g ($9.2 \cdot 10^{-4}$ mol) of 1,5-cyclooctadiene were added to the distillation residue from Example 2 and a mixture of 23.7 g (0.25 mol) of chlorodimethylsilane and 0.1 g ($9.2 \cdot 10^{-4}$ mol) of 1,5-cyclooctadiene was again introduced. The reaction was carried out in a manner analogous to Example 1. The yield after distillation was 37.0 g (87%).

EXAMPLE 4
(Embodiment II)

The procedure was analogous to that of Example 1. In addition, 10.0 g (0.06 mol) of chloro(3-chloropropyl)dimethylsilane were placed in the reaction flask as solvent. Distillation gave 48.8 g of product. After subtraction of the 10.0 g used, the yield is 38.8 g, corresponding to a percentage yield of 91%.

EXAMPLE 5
(Embodiment III)

Using a batch size as in Example 2, chloro(3-chloropropyl)dimethylsilane, catalyst and 1,5-cyclooctadiene were placed in the reaction flask and a mixture of allyl chloride, chlorodimethylsilane and 1,5-cyclooctadiene was added dropwise. Distillation gave 50.1 g of product. After subtraction of the 10.0 g of desired product employed as solvent, the yield is 40.1 g, corresponding to a percentage yield of 94%.

EXAMPLE 6
(Comparative Example Using a Platinum Catalyst)

19.2 g (0.25 mol) of allyl chloride and 21.0 mg ($3.1 \cdot 10^{-5}$ mol, 125 ppm) of dichlorodicyclopentadieneplatinum(II) were placed in a 100 ml three-neck flask provided with a low-temperature condenser, internal thermometer and dropping funnel. At a bath temperature of 37° C., 23.7 g (0.25 mol) of chlorodimethylsilane were introduced. The mixture was allowed to react further at 50° C. for another 3 hours. Work-up by distillation gave only 18.1 g (42%) of chloro(3-chloropropyl)dimethylsilane.

EXAMPLE 7
(Comparative Example Without Addition of the Cocatalyst)

The procedure of Example 1 was used, but without addition of 1,5-cyclooctadiene. Even after a reaction time of 24 hours, no measurable reaction was found (NMR).

What is claimed is:
1. A process for preparing a silane of the formula I

which comprises reacting a silane of the formula II

with an alkene of the formula III

in the presence of an iridium compound of the formula IV as catalyst

and free diene as cocatalyst, where $R^1$, $R^2$, $R^3$ are each independently a monovalent Si—C-bonded, unsubstituted or halogen-substituted $C_1$–$C_{18}$-hydrocarbon radical, a chlorine atom or a $C_1$–$C_{18}$-alkoxy radical, $R^4$, $R^5$, $R^6$ are each independently a hydrogen atom, a monovalent $C_1$–$C_{18}$-hydrocarbon radical which is unsubstituted or optionally bears F, Cl, OR, NR'$_2$, CN or NCO substituents, a chlorine atom, a fluorine atom or a $C_1$–$C_{18}$-alkoxy radical, and where 2 radicals $R^4$, $R^5$, $R^6$ together with the carbon atoms to which they are bound may form a cyclic moiety, R is a hydrogen atom or a monovalent $C_1$–$C_{18}$-hydrocarbon radical and diene is a $C_4$–$C_{50}$-hydrocarbon compound which is unsubstituted or optionally bears F, Cl, OR, $NR'_2$, CN or NCO as substituents, and has at least two ethylenic C=C double bonds.

2. The process of claim 1, wherein $R^1$, $R^2$, and $R^3$ independently are $C_1$–$C_6$-alkyl radicals or $C_1$–$C_6$-alkoxy radicals.

3. The process of claim 1, wherein $R^5$ and $R^6$ independently are $C_1$–$C_6$-alkyl radicals or $C_1$–$C_6$-alkoxy radicals.

4. The process of claim 2, wherein $R^5$ and $R^6$ independently are $C_1$–$C_6$-alkyl radicals or $C_1$–$C_6$-alkoxy radicals.

5. The process of claim 1, wherein $R^4$ is selected from among the radicals hydrogen, methyl, ethyl.

6. The process of claim 2, wherein $R^4$ is selected from among the radicals hydrogen, methyl, ethyl.

7. The process of claim 3, wherein $R^4$ is selected from among the radicals hydrogen, methyl, ethyl.

8. The process of claim 1, wherein the temperature is from 0° C. to 300° C.

9. The process of claim 1, wherein superatmospheric pressure up to 100 bar is employed.

10. The process of claim 1, wherein the catalyst of the formula IV used is [(cycloocta-1c,5c-diene)IrCl]$_2$.

11. The process of claim 2, wherein the catalyst of the formula IV used is [(cycloocta-1c,5c-diene)IrCl]$_2$.

12. The process of claim 3, wherein the catalyst of the formula IV used is [(cycloocta-1c,5c-diene)IrCl]$_2$.

13. The process of claim 1, wherein the cocatalyst used is 1,5-cyclooctadiene.

14. The process of claim 10, wherein the cocatalyst used is 1,5-cyclooctadiene.

15. The process of claim 1, wherein further diene is continuously introduced as cocatalyst during said reacting.

16. The process of claim 15, wherein said further diene is introduced in a continuous manner.

17. The process of claim 1, wherein said diene is a cyclic diene.

18. The process of claim 16, wherein said diene is a cyclic diene.

* * * * *